(12) United States Patent
Lee et al.

(10) Patent No.: US 7,173,163 B2
(45) Date of Patent: *Feb. 6, 2007

(54) METHODS FOR PRODUCING TRANSGENIC PLANTS WITH ENHANCED RESISTANCE AND DECREASED UPTAKE OF HEAVY METALS

(75) Inventors: Youngsook Lee, Pohang (KR); Young-Yell Yang, Pohang (KR); Inhwan Hwang, Pohang (KR); Hyunjoo Bae, Daegu (KR); Joohyun Lee, Seoul (KR); Enrico Martinoia, Zürich (CH)

(73) Assignees: Posco, Pohang-shi (KR); Postech Foundation, Pohang-shi (KR)

( * ) Notice: Subject to any disclaimer, the term of this patent is extended or adjusted under 35 U.S.C. 154(b) by 98 days.

This patent is subject to a terminal disclaimer.

(21) Appl. No.: 10/474,290

(22) PCT Filed: Apr. 4, 2002

(86) PCT No.: PCT/KR02/00605

§ 371 (c)(1),
(2), (4) Date: Oct. 1, 2003

(87) PCT Pub. No.: WO02/081707

PCT Pub. Date: Oct. 17, 2002

(65) Prior Publication Data

US 2004/0098759 A1      May 20, 2004

(30) Foreign Application Priority Data

Apr. 4, 2001 (KR) ............................ 2001-0017837
Apr. 4, 2002 (KR) ............................ 2002-0018369

(51) Int. Cl.
*C12N 15/09* (2006.01)
*C12N 15/31* (2006.01)
*C12N 15/82* (2006.01)
*A01H 5/00* (2006.01)

(52) U.S. Cl. .................. 800/278; 800/298; 435/320.1; 435/468; 435/430.1

(58) Field of Classification Search ................ 800/278, 800/298, 295; 435/468, 320.1, 430.1
See application file for complete search history.

(56) References Cited

FOREIGN PATENT DOCUMENTS

| EP | 1136558 A1 | 9/2001 |
|----|------------|--------|
| WO | WO 97/45000 | 12/1997 |
| WO | WO99/61616 | 12/1999 |
| WO | WO 00/04760 | 2/2000 |

OTHER PUBLICATIONS

Peter Goldbrough. Ann Arbor Press, pp. 221-228, 1999.*
Fox and Guerinot et al. Annu. Rev. Plant Physiol. Plant Molec. Biol., vol. 49, pp. 669-696 (1998).*
Axelsen and Palmgren, J Mol Evol., 1998; 46:84-101.
Rensing et al., "The zntA gene of *Escherichia coli* encodes a Zn(II)-translocating P-type ATPase", Proc. Natl. Acad. Sci. USA, Dec. 1997; 94:14326-14331.
Lee et al., "Functional Expression of a Bacterial Heavy Metal Transporter in Arabidopsis Enhances Resistance to and Decrease Uptake of Heavy Metals", Plant Physiology, Oct. 2003; 133:589-596.
Sharma et al., "The ATP Hydrolytic Activity of Purified ZntA, a Pb(II)/Cd(II)/Zn(II)-translocating ATPase from *Escherichia coli*", The Journal of Biological Chemistry (2000), 275(6):3873-3878.

* cited by examiner

*Primary Examiner*—Medina A. Ibrahim
(74) *Attorney, Agent, or Firm*—JHK Law; Joseph Hyosuk Kim

(57) ABSTRACT

The present invention relates to a method of producing transformants with enhanced resistance and decreased uptake of heavy metals, and a plant transformed with a P type ATPase ZntA gene that pumps out heavy metals from the cells. The transformants show better growth than wild type in environment contaminated with heavy metals and have lower heavy metal contents than wild type plants. Therefore, this method of transforming plants with ZntA or biologically active ZntA—like heavy metal pumping ATPases can be useful for developing plants for phytoremediation and also for a safe crop that has resistance to heavy metals and low heavy metal contents.

18 Claims, 10 Drawing Sheets

(a)

(b)

(c)

(d)

Pb²⁺ 0.7mM

Cd²⁺ 70 uM

Pb²⁺ 0.7mM

Cd²⁺ 70 uM

SEQUENCE LISTING

<160> NUMBER OF SEQ ID NOS: 6

<210> SEQ ID NO 1
<211> LENGTH: 2199
<212> TYPE: DNA
<213> ORGANISM: Escherichia coli
<220> FEATURE:
<221> NAME/KEY: zntA gene
<222> LOCATION: (1)..(2199)

<400> SEQUENCE: 1

```
atgtcgactc ctgacaatca cggcaagaaa gcccctcaat tgctgcgtt caaaccgcta      60 accacggtac agaacgccaa cgactgttgc tgcgacggcg catgttccag cacgccaact     120
ctctctgaaa acgtctccgg cacccgctat agctggaaag tcagcggcat ggactgcgcc     180
gcctgtgcgc gcaaggtaga aaatgccgtg cgccagcttg caggcgtgaa tcaggtgcag     240
gtgttgttcg ccaccgaaaa actggtggtc gatgccgaca atgacattcg tgcacaagtt     300
gaatctgcgc tgcaaaaagc aggctattcc ctgcgcgatg aacaggccgc cgaagaaccg     360
caagcatcac gcctgaaaga gaatctgccg ctgattacgc taatcgtgat gatggcaatc     420
agctggggtc tggagcagtt caatcatccg ttcgggcaac tggcgtttat cgcgaccacg     480
ctggttgggc tgtacccgat tgctcgtcag gcattacggt tgatcaaatc cggcagctac     540
ttcgccattg aaaccttaat gagcgtagcc gctattggtg cactgtttat tggcgcaacg     600
gctgaagctg cgatggtgtt gctgctgttt ttgattggtg aacgactgga aggctgggcc     660
gccagccgcg cgcgtcaggg cgttagcgcg ttaatgcgc tgaaaccaga aaccgccacg     720
cgcctgcgta agggtgagcg ggaagaggtg gcgattaaca gcctgcgccc tggcgatgtg     780
attgaagtcg ccgcaggtgg gcgtttgcct gccgacggta aactgctctc accgtttgcc     840
agttttgatg aaagcgccct gaccggcgaa tccattccgg tggagcgcgc aacgggcgat     900
aaagtccctg ctggtgccac cagcgtagac cgtctggtga cgttggaagt gctgtcagaa     960
ccgggagcca gcgccattga ccggattctg aaactgatcg aagaagccga agagcgtcgc    1020
gctcccattg agcggtttat cgaccgtttc agccgtatct atacgcccgc gattatggcc    1080
gtcgctctgc tggtgacgct ggtgccaccg ctgctgtttg ccgccagctg gcaggagtgg    1140
atttataaag ggctgacgct gctgctgatt ggctgcccgt gtgcgttagt tatctcaacg    1200
cctgcggcga ttacctccgg gctggcggcg gcagcgcgtc gtgggcgtt gattaaaggc    1260 ggagcggcgc tggaacagct gggtcgtgtt actcaggtgg cgtttgataa aaccggtacg    1320
ctgaccgtcg gtaaaccgcg cgttaccgcg attcatccgg caacgggtat tagtgaatct    1380
gaactgctga cactggcggc ggcggtcgag caaggcgcga cgcatccact ggcgcaagcc    1440
```

-continued

```
atcgtacgcg aagcacaggt tgctgaactc gccattccca ccgccgaatc acagcgggcg   1500
ctggtcgggt ctggcattga agcgcaggtt aacggtgagc gcgtattgat ttgcgctgcc   1560
gggaaacatc ccgctgatgc atttactggt ttaattaacg aactggaaag cgccgggcaa   1620
acggtagtgc tggtagtacg taacgatgac gtgcttggtg tcattgcgtt acaggatacc   1680
ctgcgcgccg atgctgcaac tgccatcagt gaactgaacg cgctgggcgt caaaggggtg   1740
atcctcaccg gcgataatcc acgcgcagcg gcggcaattg ccggggagct ggggctggag   1800
tttaaagcgg gcctgttgcc ggaagataaa gtcaaagcgg tgaccgagct gaatcaacat   1860
gcgccgctgg cgatggtcgg tgacggtatt aacgacgcgc agcgatgaa agctgccgcc    1920 atcgggattg caatgggtag cggcacagac gtggcgctgg aaaccgccga cgcagcatta   1980
acccataacc acctgcgcgg cctggtgcaa atgattgaac tggcacgcgc cactcacgcc   2040
aatatccgcc agaacatcac tattgcgctg gggctgaaag ggatcttcct cgtcaccacg   2100
ctgttaggga tgaccgggtt gtggctggca gtgctggcag atacgggggc gacggtgctg   2160
gtgacagcga atgcgttaag attgttgcgc aggagataa                          2199
```

<210> SEQ ID NO 2
<211> LENGTH: 732
<212> TYPE: PRT
<213> ORGANISM: Escherichia coli
<220> FEATURE:
<221> NAME/KEY: ZntA protein
<222> LOCATION: (1)..(732)

<400> SEQUENCE: 2

```
Met Ser Thr Pro Asp Asn His Gly Lys Lys Ala Pro Gln Phe Ala Ala
1               5                   10                  15

Phe Lys Pro Leu Thr Thr Val Gln Asn Ala Asn Asp Cys Cys Cys Asp
                20                  25                  30

Gly Ala Cys Ser Ser Thr Pro Thr Leu Ser Glu Asn Val Ser Gly Thr
            35                  40                  45

Arg Tyr Ser Trp Lys Val Ser Gly Met Asp Cys Ala Ala Cys Ala Arg
        50                  55                  60

Lys Val Glu Asn Ala Val Arg Gln Leu Ala Gly Val Asn Gln Val Gln
65                  70                  75                  80

Val Leu Phe Ala Thr Glu Lys Leu Val Val Asp Ala Asp Asn Asp Ile
                85                  90                  95

Arg Ala Gln Val Glu Ser Ala Leu Gln Lys Ala Gly Tyr Ser Leu Arg
            100                 105                 110

Asp Glu Gln Ala Ala Glu Glu Pro Gln Ala Ser Arg Leu Lys Glu Asn
        115                 120                 125

Leu Pro Leu Ile Thr Leu Ile Val Met Met Ala Ile Ser Trp Gly Leu
    130                 135                 140

Glu Gln Phe Asn His Pro Phe Gly Gln Leu Ala Phe Ile Ala Thr Thr
145                 150                 155                 160

Leu Val Gly Leu Tyr Pro Ile Ala Arg Gln Ala Leu Arg Leu Ile Lys
                165                 170                 175

Ser Gly Ser Tyr Phe Ala Ile Glu Thr Leu Met Ser Val Ala Ala Ile
            180                 185                 190

Gly Ala Leu Phe Ile Gly Ala Thr Ala Glu Ala Ala Met Val Leu Leu
        195                 200                 205

Leu Phe Leu Ile Gly Glu Arg Leu Glu Gly Trp Ala Ala Ser Arg Ala
    210                 215                 220
```

-continued

```
Arg Gln Gly Val Ser Ala Leu Met Ala Leu Lys Pro Glu Thr Ala Thr
225                 230                 235                 240

Arg Leu Arg Lys Gly Arg Glu Glu Val Ala Ile Asn Ser Leu Arg
            245                 250                 255

Pro Gly Asp Val Ile Glu Val Ala Ala Gly Arg Leu Pro Ala Asp
                260                 265                 270

Gly Lys Leu Leu Ser Pro Phe Ala Ser Phe Asp Glu Ser Ala Leu Thr
        275                 280                 285

Gly Glu Ser Ile Pro Val Glu Arg Ala Thr Gly Asp Lys Val Pro Ala
        290                 295                 300

Gly Ala Thr Ser Val Asp Arg Leu Val Thr Leu Glu Val Leu Ser Glu
305                 310                 315                 320

Pro Gly Ala Ser Ala Ile Asp Arg Ile Leu Lys Leu Ile Glu Glu Ala
                325                 330                 335

Glu Glu Arg Arg Ala Pro Ile Glu Arg Phe Ile Asp Arg Phe Ser Arg
            340                 345                 350

Ile Tyr Thr Pro Ala Ile Met Ala Val Ala Leu Leu Thr Leu Val
                355                 360                 365

Pro Pro Leu Leu Phe Ala Ala Ser Trp Gln Glu Trp Ile Tyr Lys Gly
370                 375                 380

Leu Thr Leu Leu Leu Ile Gly Cys Pro Cys Ala Leu Val Ile Ser Thr
385                 390                 395                 400

Pro Ala Ala Ile Thr Ser Gly Leu Ala Ala Ala Arg Arg Gly Ala
                405                 410                 415

Leu Ile Lys Gly Gly Ala Ala Leu Glu Gln Leu Gly Arg Val Thr Gln
                420                 425                 430

Val Ala Phe Asp Lys Thr Gly Thr Leu Thr Val Gly Lys Pro Arg Val
            435                 440                 445

Thr Ala Ile His Pro Ala Thr Gly Ile Ser Glu Ser Glu Leu Leu Thr
450                 455                 460

Leu Ala Ala Ala Val Glu Gln Gly Ala Thr His Pro Leu Ala Gln Ala
465                 470                 475                 480

Ile Val Arg Glu Ala Gln Val Ala Glu Leu Ala Ile Pro Thr Ala Glu
                485                 490                 495

Ser Gln Arg Ala Leu Val Gly Ser Gly Ile Glu Ala Gln Val Asn Gly
            500                 505                 510

Glu Arg Val Leu Ile Cys Ala Ala Gly Lys His Pro Ala Asp Ala Phe
        515                 520                 525

Thr Gly Leu Ile Asn Glu Leu Glu Ser Ala Gly Gln Thr Val Val Leu
        530                 535                 540

Val Val Arg Asn Asp Asp Val Leu Gly Val Ile Ala Leu Gln Asp Thr
545                 550                 555                 560

Leu Arg Ala Asp Ala Ala Thr Ala Ile Ser Glu Leu Asn Ala Leu Gly
                565                 570                 575

Val Lys Gly Val Ile Leu Thr Gly Asp Asn Pro Arg Ala Ala Ala
            580                 585                 590

Ile Ala Gly Glu Leu Gly Leu Glu Phe Lys Ala Gly Leu Leu Pro Glu
            595                 600                 605

Asp Lys Val Lys Ala Val Thr Glu Leu Asn Gln His Ala Pro Leu Ala
        610                 615                 620

Met Val Gly Asp Gly Ile Asn Asp Ala Pro Ala Met Lys Ala Ala
625                 630                 635                 640

Ile Gly Ile Ala Met Gly Ser Gly Thr Asp Val Ala Leu Glu Thr Ala
```

```
                    645                 650                 655
Asp Ala Ala Leu Thr His Asn His Leu Arg Gly Leu Val Gln Met Ile
            660                 665                 670
Glu Leu Ala Arg Ala Thr His Ala Asn Ile Arg Gln Asn Ile Thr Ile
            675                 680                 685
Ala Leu Gly Leu Lys Gly Ile Phe Leu Val Thr Thr Leu Leu Gly Met
            690                 695                 700
Thr Gly Leu Trp Leu Ala Val Leu Ala Asp Thr Gly Ala Thr Val Leu
705                 710                 715                 720
Val Thr Ala Asn Ala Leu Arg Leu Leu Arg Arg Arg
                725                 730

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
ggatccaaag agtaaagaag aacaatgtcg actcctgaca at                    42

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
ggatccctct cctgcgcaac aatct                                        25

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gagatgtcga gtctcgaa                                                18

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ctcgagcaca gtgtagtgac tgg                                          23
```

METHODS FOR PRODUCING TRANSGENIC PLANTS WITH ENHANCED RESISTANCE AND DECREASED UPTAKE OF HEAVY METALS

This application is a 371 of PCT/KR02/00605 filed April 4, 2002.

BACKGROUND OF THE INVENTION (a) Field of the Invention

The present invention relates to a method of producing transformants with enhanced heavy metal resistance. More particularly, the present invention relates to transgenic plants that have an improved growth but decreased heavy metal contents when grown in environment contaminated with heavy metals, thus this method can be used for developing plants for phytoremediation and also for developing safe crops.

(b) Description of the Related Art

Heavy metals are major environmental toxicants, which cause reactive oxidation species generation, DNA damage, and enzyme inactivation by binding to active sites of enzymes in cells.

Contamination of the environment with heavy metals has increased drastically due to industrialization. By the early 1990s, the worldwide annual release had reached 22,000 tons of cadmium, 954,000 tons of copper, 796,000 tons of lead, and 1,372,000 tons of zinc (Alloway B J & Ayres D C (1993) Principles of environmental pollution. Chapman and Hall, London). The soils contaminated with heavy metal inhibit normal plant growth and cause contamination of foodstuffs. Many heavy metals are very toxic to human health and carcinogenic at low concentrations. Therefore removal of heavy metals from the environment is an urgent issue.

Studies for removing heavy metals from soil are very actively progressing worldwide. Traditional methods of dealing with soil contaminants include physical and chemical approaches, such as the removal and burial of the contaminated soil, isolation of the contaminated area, fixation (chemical processing of the soil to immobilize the metals), and leaching using an acid or alkali solution (Salt D E, Blaylock M, Kumar N P B A, Viatcheslav D, Ensley B D, et al. (1995). Phytoremediation: a novel strategy for the removal of toxic metals from the environment using plants. *Bio-Technology* 13,468–74; Raskin I, Smith R D, Salt D E. (1997) Phytoremediation of metals: using plants to remove pollutants from the environment. *Curr. Opin. Biotechnol.* 8, 221–6). These methods, however, are costly and energy-intensive processes.

Phytoremediation has recently been proposed as a low-cost, environment-friendly way to remove heavy metals from contaminated soils, and is a relatively new technology for cleanup of contaminated soil that uses general plants, specially bred plants, or transgenic plants to accumulate, remove, or detoxify environmental contaminants. The phytoremediation technology is divided into phytoextraction, rhizofiltration, and phytostabilization.

Phytoextraction is a method using metal-accumulating plants to extract metals from soil into the harvestable parts of the plants; rhizofiltration is a method using plant roots to remove contaminants from polluted aqueous streams; and phytostabilization is the stabilization of contaminants such as toxic metals in soils to prevent their entry into ground water, also with plants (Salt et al., *Biotechnology* 13(5): 468–474, 1995).

Examples of phytoremediation are methods using the plants of *Larrea tridentate* species that are particularly directed at the decontamination of soils containing copper, nickel, and cadmium (U.S. Pat. No. 5,927,005), and a method using Brassicaceae family (Baker et al., *New Phytol.* 127:61–68, 1994).

In addition, phytoremediation using transgenic plants that are generated by introducing genes having resistant activity for heavy metals have been attempted. Examples of heavy metal resistant genes are CAX2 (Calcium exchanger 2), cytochrome P450 2E1, NtCBP4 (Nicotiana tabacum calmodulin-binding protein), GSHII (glutathione synthetase), merB (organomercurial lyase), and MRT polypeptide (metal-regulated transporter polypeptide).

CAX2 (Calcium exchanger 2), isolated from *Arabidopsis thaliana*, accumulates heavy metals including cadmium and manganese in plants (Hirschi et al., *Plant Physiol.* 124: 125–134, 2000). Cytochrome P450 2E1 uptakes and decomposes organic compounds such as trichloroethylene (Doty SL et al., *Proc. Natl. Acad. Sci. USA* 97:6287–6291, 2000). *Nicotiana tabacum* transformed with NtCBP4 has resistant activity for nickel (Arazi et al., *Plant J.* 20:171–182, 1999), GSHII accumulates cadmium (Liang et al., *Plant Physiol.* 119:73–80,1999), merB detoxifies organic mercury (Bizily et al., *Proc. Natl. Acad. Sci. USA* 96:6808–6813, 1999), and MRT polypeptide removes heavy metals including cadmium, zinc, and manganese from contaminated soil (U.S. Pat. No. 5,846,821).

However, the transgenic plants generated by introducing the above-mentioned genes have limitations in growth due to accumulation of heavy metals, and they can produce contaminated fruits and crops, when grown in contaminated soil. Therefore, there is a need for plants that have a lower uptake of heavy metals than the wild type, and that maintain healthy growth even in an environment contaminated with heavy metals.

SUMMARY OF THE INVENTION

It is an object of the invention to provide a gene, when expressed in plants, that confers heavy metal resistance and that can inhibit accumulation of heavy metals.

It is a further object of the invention to provide a recombinant vector harboring a heavy metal resistant gene.

It is a further object of the invention to provide a method for producing transformants that have heavy metal resistance and that accumulate less heavy metals than wild type plants.

It is a further object of the invention to provide transformants that have heavy metal resistance and that accumulate less heavy metals than wild type plants.

It is a further object of the invention to provide a method of transforming a polluted area into an environmentally friendly space.

To accomplish the aforementioned objects, the invention provides a recombinant vector containing a coding sequence for a heavy metal-transporting P type ATPase, wherein the coding sequence is operably linked to and under the regulatory control of a plant-expressible transcription and translation regulatory sequence.

Also, the invention provides a transgenic plant, or parts thereof, each transformed with a recombinant vector.

Also, the invention provides a transgenic plant cell.

Also, the invention provides a transgenic plant, stably transformed with a recombinant vector.

Also, the invention provides a recombinant vector comprising a coding sequence for a heavy metal-transporting P type ATPase, ZntA of SEQ ID NO: 1;

wherein the coding sequence is operably linked to and under the regulatory control of a plant-expressible transcription and translation regulatory sequence; and wherein the ZntA contains an approximately 100 amino acid residue N-terminal extension domain, a first transmembrane spanning domain, a second transmembrane spanning domain containing a putative cation channel motif CPX domain, a third transmembrane spanning domain, a first cytoplasmic domain, a second cytoplasmic domain, and a C-terminal domain Also, the invention provides a recombinant vector comprising a coding sequence for a heavy metal-transporting P type ATPase, ZntA wherein the coding sequence is operably linked to and under the regulatory control of a plant-expressible transcription and translation regulatory;

wherein the ZntA contains an approximately 100 amino acid residue N-terminal extension domain, a first transmembrane spanning domain, a second transmembrane spanning domain containing a putative cation channel motif CPX domain, a third transmembrane spanning domain, a first cytoplasmic domain, a second cytoplasmic domain, and a C-terminal domain; and wherein each of the domains of the coding sequence shares at least about 50% homology with a same domain of SEQ ID NO:1.

Also, the invention provides a method of producing a transgenic plant with enhanced resistance to heavy metals comprising:

(a) preparing an expression construct comprising a sequence encoding a heavy metal-transporting P type ATPase, operably linked to and under the regulatory control of a plant-expressible transcription and translation regulatory sequence;

(b) preparing a recombinant vector harboring the expression construct; and (c) introducing the expression construct of the recombinant vector into a plant cell or plant tissue to produce a transgenic plant cell or transgenic plant tissue

DETAILED DESCRIPTION OF THE PREFERRED EMBODIMENTS

Figure 1:
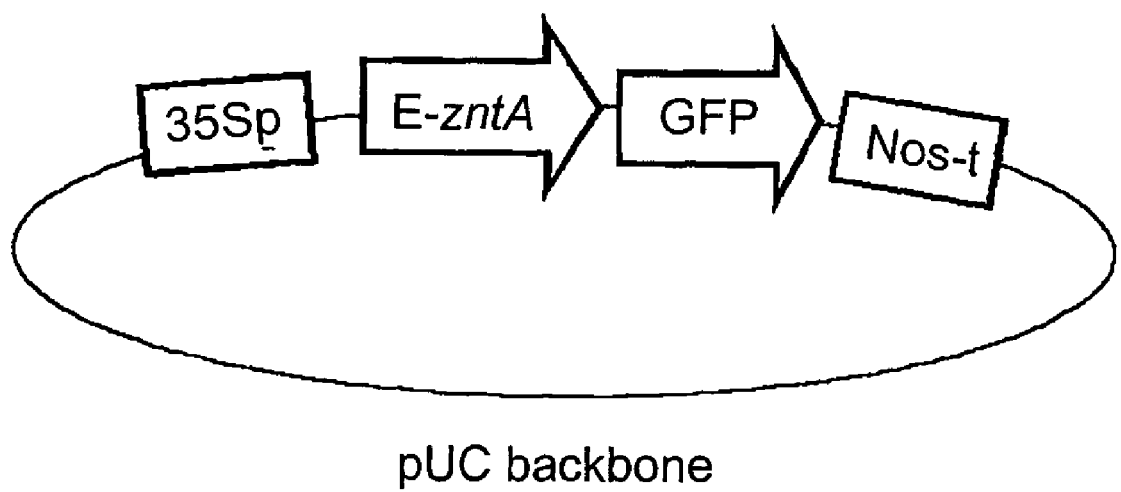
FIG. 1 represents the map of the recombinant vector pEZG.

As used herein, the term "P type ATPase" refers to a transporter that transports a specific material by using energy from ATP hydrolysis and that forms a phosphorylated intermediate. More particularly, the P type ATPase is a heavy metal-transporting ATPase. The heavy metal is a metal element having a specific gravity over 4 including arsenic (As), antimony (Sb), lead (Pb), mercury (Hg), cadmium (Cd), chrome, tin (Sn), zinc, barium (Ba), nickel (Ni), bismuth (Bi), cobalt (Co), manganese (Mn), iron (Fe), copper (Cu), and vanadium (V).

ZntA is a P type ATPase of *E. coli* (Rensing C, Mitra B, Rosen B P. (1997) *Proc. Natl. Acad. Sci.* USA. 94,14326–31; Sharma, R., Rensing, C., Rosen, B. P., Mitra, B. (2000) *J Biol. Chem.* 275,3873–8) which pumps Pb(II)/Cd(II)/Zn(II) across the plasma membrane.

P-type ATPases typically have 2 large cytoplasmic domains and 6 transmembrane domains. ZntA has similar domains, and in addition, 2 more transmembrane helixes at N-terminus and N-terminal extension of about 100 amino acids containing CXXC motif. The first large cytoplasmic domain of ZntA is about 145 amino acid long and involved in hydrolysis of phosphointermediate, and the second large cytoplasmic domain is 280 amino acid long and has a phosphorylation motif. We denote the 4 transmembrane helixes of the N-terminal side as the first transmembrane spanning domain. The 2 transmembrane helixes between the 2 large cytoplasmic domains is denoted as the second transmembrane spanning domain. This domain contains a putative cation channel motif CPX domain. The transmembrane helixes between the second large cytoplasmic domain and the c-terminus is denoted as the third transmembrane spanning domain. The cytoplasmic domain following the third transmembrane spanning domain is denoted as the C-terminal domain of ZntA.

The term "homology" refers to the sequence similarity between 2 DNA or protein molecules. "Biologically active ZntA-like heavy metal pumping ATPases" are coded by DNA sequences which have at least 50% homology to ZntA, and have heavy metal pumping activity. Biologically active ZntA-like heavy metal pumping ATPases include zinc-transporting ATPase (NC_000913), zinc-transporting ATPase (NC_002655), heavy metal-transporting ATPase (NC_003198), P-type ATPase family (NC_003197), cation transporting P-type ATPase from *Mycobacterium lepraed* (GenBank #Z46257), and many others.

A "heavy metal resistance protein" is a protein capable of mediating resistance to at least one heavy metal, including, but not limited to, lead, cadmium, and zinc. An example of a heavy metal resistance protein is ZntA protein of SEQ ID NO:2.

The term "plant-expressible" means that the coding sequence is operably linked to and under the regulatory control of a transcription and translation regulatory sequence that can be efficiently expressed by plant cells, tissues, parts and whole plants.

"Plant-expressible transcriptional and translational regulatory sequences" are those which can function in plants, plant tissues, plant parts and plant cells to effect the transcriptional and translational expression of the target sequence with which they are associated. Included are 5' sequences of a target sequence to be expressed, which qualitatively control gene expression (turn gene expression on or off in response to environmental signals such as light, or in a tissue-specific manner); and quantitative regulatory sequences which advantageously increase the level of downstream gene expression. An example of a sequence motif that serves as a translational control sequence is that of the ribosome binding site sequence. Polyadenylation signals are examples of transcription regulatory sequences positioned downstream of a target sequence, and there are several that are well known in the art of plant molecular biology.

A "transgenic plant" is one that has been genetically modified, unlike the wild type plants. Transgenic plants typically express heterologous DNA sequences, which confer the plants with characters different from that of wild type plants. As specifically exemplified herein, a transgenic plant is genetically modified to contain and express at least one heterologous DNA sequence that is operably linked to and under the regulatory control of transcriptional control sequences which function in plant cells or tissue, or in whole plants.

The present invention provides a plant-expressible expression construct containing a coding sequence for a heavy metal-transporting ATPase protein. The coding sequence is operably linked to and under the regulatory control of a plant-expressible transcription and translation regulatory sequence. The heavy metals include arsenic (As), antimony (Sb), lead (Pb), mercury (Hg), cadmium (Cd), chrome, tin (Sn), zinc, barium (Ba), nickel (Ni), bismuth (Bi), cobalt (Co), manganese (Mn), iron (Fe), copper (Cu) and vanadium (V).

The expression construct includes a promoter, a heavy metal-transporting P type ATPase gene, and a transcriptional terminator. The suitable plant-expressible promoters include the 35S or 19S promoters of Cauliflower Mosaic Virus; the nos (nopaline synthase), ocs (octopine synthase), or mas (mannopine synthase) promoters of *Agrobacterium tumefaciens* Ti plasmids; and others known to the art.

The heavy metal-transporting ATPase gene of the present invention prefers genes encoding ZntA (SEQ ID NO:1) or biologically active ZntA-like heavy metal pumping ATPase genes, which have at least 50% homology to ZntA, and which code for proteins with heavy metal pumping activities.

The heavy metal-transporting ATPase gene of the present invention also prefers DNA sequences containing an approximately 100 amino acid residue N-terminal extension domain, a first transmembrane spanning domain, a second transmembrane spanning domain containing a putative cation channel motif CPX domain, a third transmembrane spanning domain, a first cytoplasmic domain, a second cytoplasmic domain, and a C-terminal domain of ZntA, or DNA sequences which share at least 50% homology with abovementioned domains of the biologically active ZntA-like heavy metal pumping ATPase genes.

The expression construct of the present invention may further contain a marker allowing selection of transformants in the plant cell or showing a localization of a target protein. The examples of a marker are genes carrying resistance to an antibiotic such as kanamycin, hygromycin, gentamicin, and bleomycin; and genes coding GUS ($\alpha$-glucuronidase), CAT (chloramphenicol acetyltransferase), luciferase, and GFP (green fluorescent protein). The marker allows for selection of successfully transformed plant cells growing in a medium containing certain antibiotics because they will carry the expression construct with the resistance gene to the antibiotic.

Also, the invention provides a recombinant vector comprising the expression construct. The recombinant vector comprises a backbone of the common vector and the expression construct. The common vector is preferably selected from the group consisting of pROKII, pBI76, pET21, pSK (+), pLSAGPT, pBI121, and PGEM. Examples of the prepared recombinant vector are PBI121/zntA and pEZG. PBI121/zntA comprises a backbone of PBI121, CMV 35S promoter, zntA gene, and nopaline synthase terminator; and pEZG comprises a backbone of pUC, CMV 35S promoter, zntA gene, green fluorescence protein, and nopaline synthase terminator.

Also, the present invention provides a transformant containing the expression construct. The transformant contains a DNA sequence encoding a heavy metal-transporting P type ATPase, wherein the coding sequence is operably linked to and under the regulatory control of a transcription and translation regulatory sequence.

The transformant is preferably a plant, and more preferably a plant, parts thereof, and plant cell. The plant parts include a seed. The plants are herbaceous plants and trees, and they include flowering plants, garden plants, an onion, a carrot, a cucumber, an olive tree, a sweet potato, a potato, a cabbage, a radish, lettuce, broccoli, *Nicotiana tabacum*, *Petunia hybrida*, a sunflower, *Brassica juncea*, turf, *Arabidopsis thaliana*, *Brassica campestris*, *Betula platyphylla*, a poplar, a hybrid poplar, and *Betula schmidtii*.

Techniques for generating transformants are well known. An example is *Agrobacterium tumefaciens*-mediated DNA transfer. Preferably, recombinant *A. tumefaciens* generated by electroporation, micro-particle injection, or with a gene gun can be used.

In addition, the invention provides a method of producing a transgenic plant with enhanced resistance to heavy metals, comprising:

(a) preparing an expression construct comprising a plant-expressible sequence encoding a heavy metal-transporting P type ATPase, operably linked to and under the regulatory control of a transcription and translation regulatory sequence;

(b) preparing a recombinant vector harboring the expression construct; and (c) introducing the expression construct of the recombinant vector into a plant cell or plant tissue to produce a transgenic plant cell or transgenic plant tissue.

The method of producing a transgenic plant further comprises a step: (d) regenerating a transgenic plant from the transgenic plant cell or transgenic plant tissue of step (c).

Figure 2:
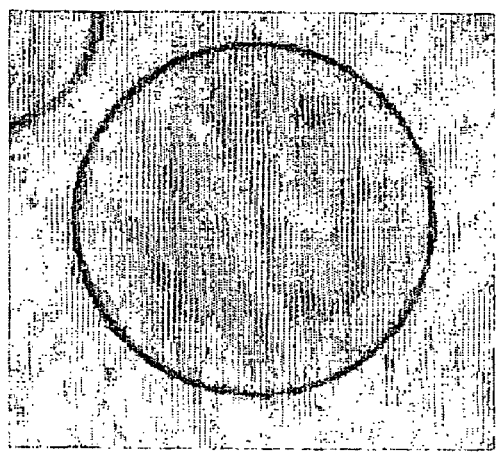
FIG. 2 shows plasma membrane localization of ZntA protein expressed in *Arabidopsis* protoplasts.
Figure 2:
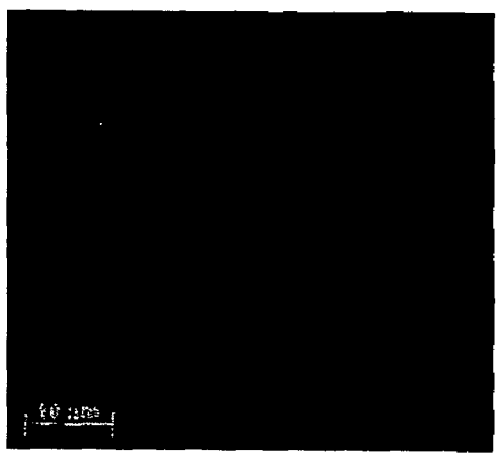
Figure 2:
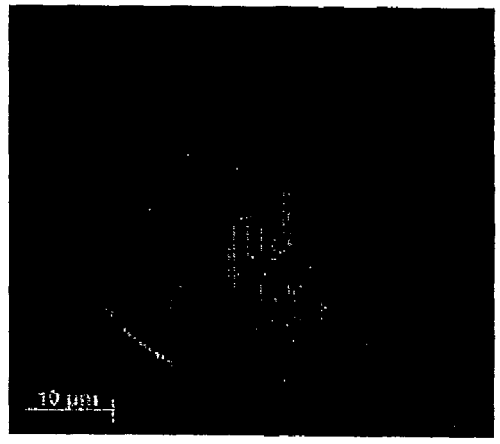
Figure 2:
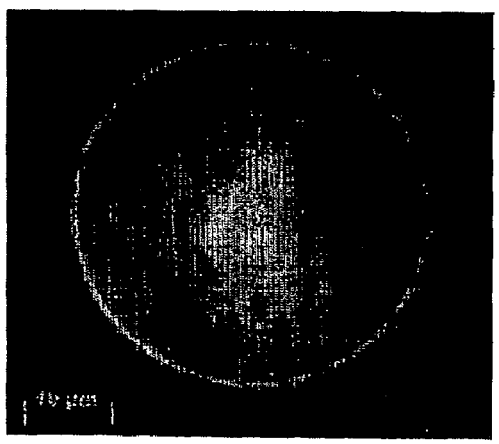
Figure 3:
FIG. 3 is a Western blot photograph showing membrane localization of ZntA protein expressed in *Arabidopsis* protoplast.

In the present invention, ZntA protein was expressed in the plasma membrane (FIGS. 2 and 3). Moreover, zntA-transgenic *Arabidopsis* plants showed enhanced resistance to lead and cadmium, and the content of lead and cadmium was lower than in a wild-type plant.

Therefore, zntA-transgenic plants or plants transformed with a gene encoding biologically active ZntA-like heavy metal pumping ATPases can grow in an environment contaminated with heavy metals, and this technique can be useful for generating crop plants with decreased uptake of harmful heavy metals. Since harmful heavy metals can be introduced into farmland inadvertently, for example, due to the yellow sand phenomenon or by natural disaster, heavy metal pumping transgenic crop plants can be a safe choice for health-concerned consumers.

The following examples are provided for illustrative purposes and are not intended to limit the scope of the invention as claimed herein. Any variations in the exemplified compositions and methods which occur to the skilled artisan are intended to fall within the scope of the present invention.

EXAMPLE 1

Isolation of ZntA Gene

*Escherichia coli* K-12 was obtained from the Korean Collection for Type Cultures of the Korea Research Institute of Bioscience and Biotechnology, and a zntA gene was cloned.

zntA was isolated by PCR using genomic DNA of *Escherichia coli* K-12 strain as a template. PCR was performed with a primer set of SEQ ID NO:4, SEQ ID NO:3, and 2.2 kb of PCR product, and zntA of SEQ ID NO:1 was obtained. The sequence of the PCR product was analyzed and the PCR product was cloned into a pGEM-T easy vector to produce pCEM-T/zntA.

EXAMPLE 2

Expression of ZntA Protein

A zntA gene was, introduced into *Arabidopsis* protoplasts, and localization of ZntA protein was investigated.

(2-1) Preparation of *Arabidopsis* Protoplasts

*Arabidopsis* protoplasts were prepared as described (Abel S, Theologis A (i 994) Transient transformation of *Arabidopsis* leaf protoplasts: a versatile experimental system to study gene expression. *Plant J.* 5, 421–7).

Seeds of *Arabidopsis* were placed into an antiseptic solution (distilled water: chlorox: 0.05% triton X-100=3:2:2), shaken for 20–30 seconds, and incubated at room temperature for 5–10 mins. The seeds were then rinsed five times with distilled water.

The *Arabidopsis* seeds were incubated in 100 ml of a liquid solution (Murashige & Skoog medium; MSMO, pH 5.7–5.8) containing vitamins, Duchefa 4.4 g/L, sucrose 20 g/L, MES (2-(N-Morpholino) Ethanesulfonic acid, Sigma) 0.5 g/L, while agitating at 120 rpm under a 16/8 hr (light/dark) cycle, at 22° C. for 2–3 weeks.

The 2–3 week-old whole plants were chopped with a razor blade to 5–10 mm² pieces. These leaf fragments were transferred to an enzyme solution (1% cellulase R-10, 0.25% marcerozyme R-10, 0.5 M mannitol, 10 mM MES, 1 mM $CaCl_2$, 5 mM β-mercaptoethanol, and 0.1% BSA, pH 5.7–5.8), vacuum-infiltrated for 10 min, and then incubated in the dark at 22° C. for 5 hours with gentle agitation at 50–75 rpm. The released protoplasts were filtered through a 100 μm mesh (Sigma S0770, USA), purified using a 21% sucrose gradient by centrifugation at 730 rpm for 10 min, and then suspended in 20 ml of W5 solution (154 mm NaCl, 125 mM $CaCl_2$, 5 mM KCl, 5 mM glucose, and 1.5 mM MES, pH 5.6) and centrifuged again at 530 rpm for 6 min. The pelleted protoplasts were re-suspended in W5 solution and kept on ice.

(2-2) Preparation of Vector pGEM-T/zntA DNA was cut with BamHI restriction enzyme and zntA genes were extracted (QIAGEN Gel extraction kit). The zntA genes were placed under the control of a Cauliflower Mosaic Virus 35S promoter, fused with and then inserted into a pUC-GFP vector containing Green Fluorescent Protein (GFP) and nopaline synthase terminator (NOS), to thereby produce pEZG.

(2-3) Preparation of Vector for H⁺ Pumping Gene

A hydrogen ion pump gene of *Arabidopsis*, AHA2 cDNA (Gene Bank: P19456), was amplified by PCR. Primers for PCR were polynucleotides of SEQ ID NO:4 and SEQ ID NO:5. PCR conditions were as follows: 94° C., 30 sec->45° C., 30 sec->72° C., 1 min, 50 cycles. The PCR product was obtained as AHA2 cDNA.

A DsRed vector (Clontech, Inc.) was treated with BgIII/NotI restriction enzyme and DsRed was obtained. The DsRed was inserted into the opened smGFP vector with a BamHI/EcI136II restriction enzyme to 326RFP. In addition, AHA2 cDNA was inserted at XmaI of the 326RFP vector and 326RFP/AHA2 was prepared.

(2-4) Introduction of pEZG or 326RFP/AHA2 Into Protoplast pEZG and 326RFP/AHA2 were introduced to the protoplasts prepared by EXAMPLE (2-1), and expression of foreign genes was confirmed.

The protoplast was centrifuged at 500 rpm for 5 min, and $5 \times 10^6$/ml of the protoplast were suspended in a MaMg solution (400 mM mannitol, 15 mM $MgCl_2$, 5 mM MES-KOH, pH 5.6). 300 μl of the suspension solution was mixed with 10 μg of pEZG and 326RFP/AHA2 respectively, which was then was added to 300 μl of PEG (400 mM mannitol, 100 mM $Ca(NO_3)_2$, 40% PEG 6000), and stored at RT for 30 min. The mixture was washed with 5 ml of W5 solution, centrifuged at 500 rpm for 3 min, and a pellet was obtained. The pellet was washed with 2 ml of W5 solution and incubated in the dark at 22–25° C. After 24 hr, expression of GFP protein was monitored and images were captured with a cooled charge-coupled device camera using a Zeiss Axioplan fluorescence microscope. The filter sets used for the GFP were XF116 (exciter, 474AF20; dichroic, 500DRLP; emitter, 510AF23) (Omega, Inc., Brattleboro, Vt.). Data were then processed using Adobe (Mountain View, Calif.) Photoshop software.

FIG. 2 shows a localization of ZntA protein fused with GFP in protoplasts transformed with pEZG and 326RFP/AHA2, respectively. "a" is control, "b" is AHA2 protein expressed in 326RFP/AHA2, "c" is ZntA protein expressed in pEZG, and "d" is an overlapped picture of "b" and "c". ZntA fused with GFP shows a green color due to GFP, and AHA2 fused with DsRed shows a red color due to DsRed.

In FIG. 2, ZntA fused with GFP was localized at the plasma membrane in *Arabidopsis* protoplasts.

In addition, membrane and cytosol fractions were isolated from *Arabidopsis* protoplasts, and Western Blot was preformed using a GFP antibody as a probe. FIG. 3 is a Western Blot photograph, wherein "WT-C" is cytosol of wild-type *Arabidopsis* protoplasts, "WT-M" is membrane of wild-type *Arabidopsis* protoplasts, "ZntA-C" is cytosol of *Arabidopsis* protoplasts transformed with pEZG, and "ZntA-M" is membrane of *Arabidopsis* protoplasts transformed with pEZG. In FIG. 3, the GFP antibody cross-reacted only with membrane proteins extracted from *Arabidopsis* protoplasts transformed with pEZG, confirming that ZntA protein was expressed in membrane.

EXAMPLE 3

Preparation of Transgenic Plants Expressing ZntA Protein.

(3-1) *Arabidopsis*

*Arabidopsis* plants were grown at 4° C. for 2 days, then they were grown with a 16/8 hr (light/dark) photoperiod, at 22° C./18° C. for 3–4 weeks until flower stalks were differentiated. The 1st flower stalk was removed, and the 2nd flower stalk was used for transformation.

(3-2) pBI121/ZntA Vector

A zntA gene was inserted into the expression vector for the plant, preparing pBI121 and pBI121/zntA.

Figure 4:
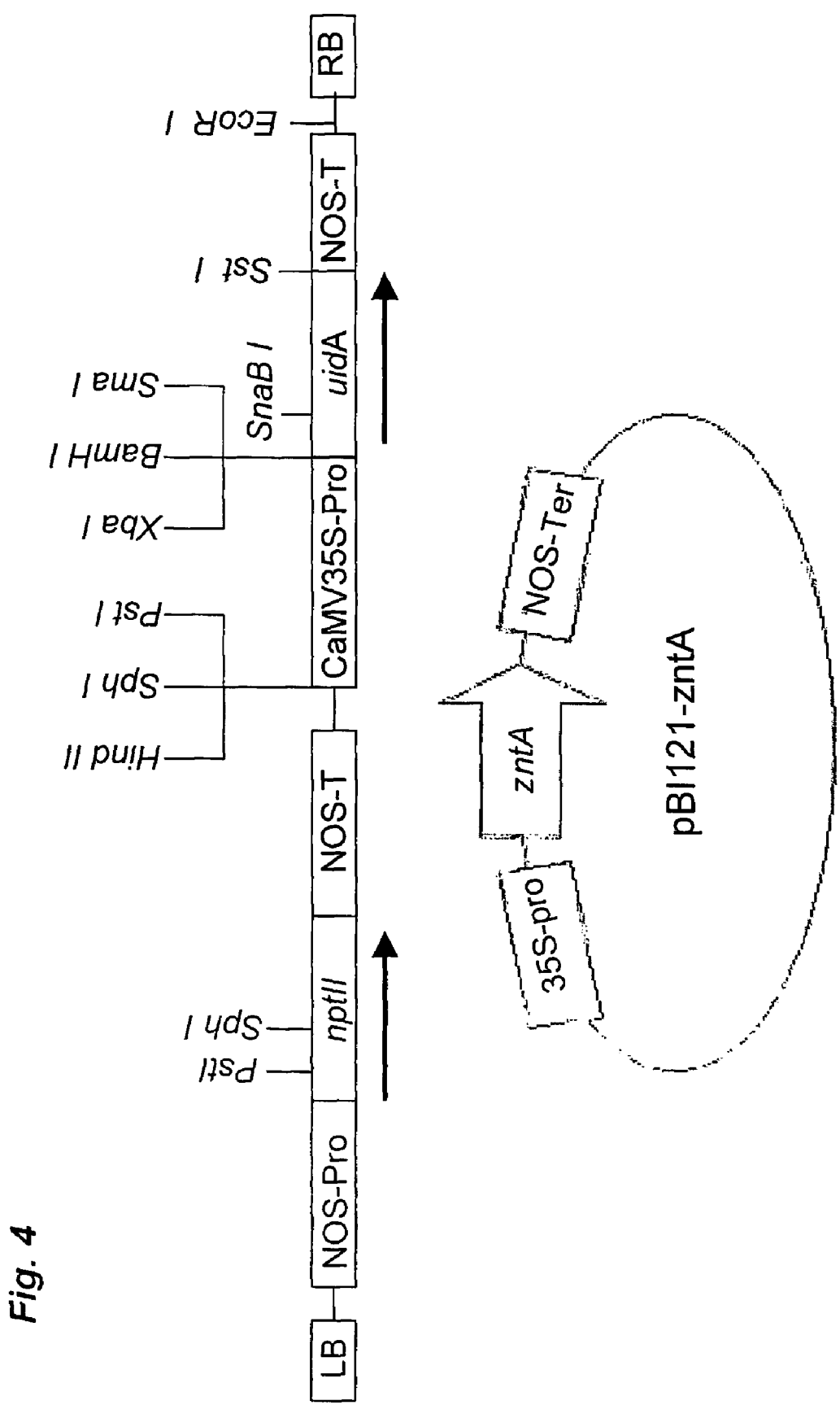
FIG. 4 represents the map of recombinant vector PBI121/zntA.

A GUS gene of pBI121 was removed by digesting with SmaI and EcI136II restriction enzymes, and a zntA gene prepared from the pGEM-T/zntA was inserted to pBI121, thereby preparing a pBI121/zntA vector (FIG. 4).

(3-3) Preparation of Transgenic Plants pBI121/zntA vector DNA was isolated with a prep-kit (Qiagen) and introduced to agrobacterium using electroporation. The agrobacterium (KCTC 10270BP) was cultured in YEP media (yeast extract 10 g, NaCl 5 g, pepton 10 g, pH 7.5) until index of O.D. reached 0.8–1.0. The culture solution was centrifuged, cells were collected and suspended in MS media (Murashige & Skoog medium, 4.3 g/L, Duchefa) containing 5% sucrose, and Silwet L-77 (LEHLE SEEDS, USA) was added as a final concentration of 0.01% just before transformation. For plant transformation, pBI121/zntA was introduced into the *Agrobacterium* LBA4404 strain, which was then used to transform *Arabidopsis* by a dipping method (Clough S J, and Bent A F (1988), Floral dip: a simplified method for *Agrobacterium*-mediated transformation of *Arabidopsis thaliana*. Plant J. 16, 735–743).

EXAMPLE 4

Selection of Transformants

For selection of plant transformed with zntA genes, plants were grown in solid Murashige-Skoog (MS) medium containing kanamycin (50 mg/l). T2 or T3 generation seeds were used for the tests. Also, a pBI121 vector was introduced to *Arabidopsis* and transformants (pBI121 plants) were selected. Seeds were obtained from wild-type *Arabidopsis*, pBI121 plants, and pBI121/zntA plants, respectively.

To test the ZntA expression level, total RNA was isolated from kanamycin-selected T2 plants and used for Northern Blot analysis. Total RNA was extracted from *Arabidopsis* plants grown on the 1/2 MS (Murashige & Skoog medium, 2.15 g/L, Duchefa)-agar media for 3 weeks. Subsequent RNA preparation and northern hybridization followed the established method (Sambrook et al. (2001) *Molecular Cloning: A laboratory manual* (Third Edition), Cold Spring Harbor Laboratory Press, Cold Spring Harbor, N.Y.) with slight modifications.

Figure 5:
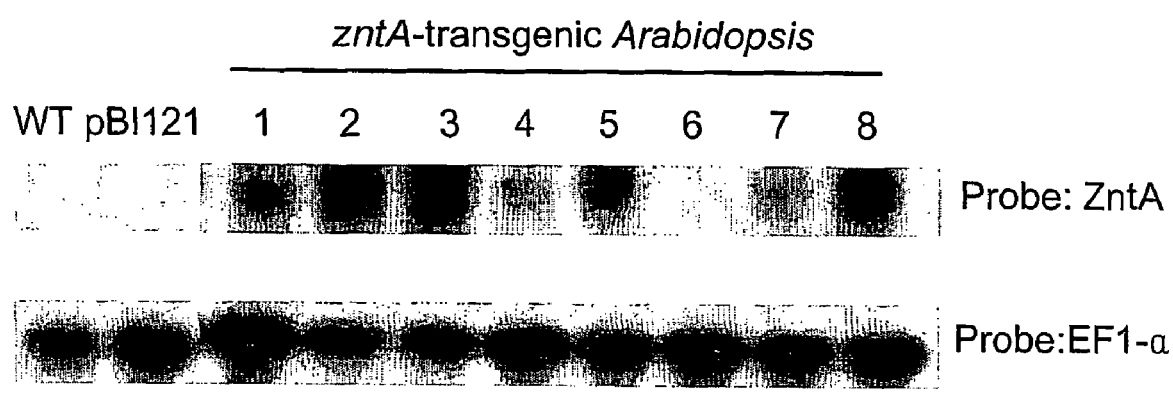
FIG. 5 is a Northern blot photograph showing expression of zntA mRNA in *Arabidopsis*.

The plant materials were frozen in liquid nitrogen and homogenized with mortars and pestles. 1 ml of TRIzol reagent (Life technology, USA) per 100 mg of tissue was added to the sample and after 5 min incubation at RT, 0.2 ml of chloroform per 1 ml of TRIzol reagent was added. After centrifugation at 10,000 g for 10 min at 4° C., the aqueous phase was taken and precipitated with 0.5 ml of isopropyl alcohol per 1 ml of TRIzol reagent and quantified by UV spectroscopy. Total RNA was separated in a formaldehyde-containing agarose gel and then transferred onto a nylon membrane. After UV crosslinking, hybridization was carried out in a modified Church buffer (7% (w/v) SDS, 0.5 M sodium phosphate (pH 7.2), 1 mM EDTA (pH 7.0)) at 68° C. overnight, with $^{32}$P-labeled zntA probes. Membranes were washed once for 10 min in 1×SSC, 0.1% SDS at room temperature, and twice for 10 min in 0.5×SSC, 0.1% SDS at 68° C. The membrane was exposed to a phosphorimager screen (Fuji film) or x-ray film (Kodak). The mRNA expression levels were analyzed by the Mac-BAS image-reader program. FIG. 5 is a Northern Blot photograph showing expression of zntA mRNA in *Arabidopsis*. Transcription of zntA RNA was not observed in wild-type *Arabidopsis* and pBI121 plants, but it was observed in pBI121/zntA plants. EF1-a is constitutively expressed in plants and its even levels indicated that the same amount of RNA was used for different samples.

EXAMPLE 5

Heavy Metals Resistance of Plant Transformed With ZntA Gene

Wild-type *Arabidopsis* plants and pBI121/zntA plants were grown in 1/2 MS-agar media for 2 weeks and transferred 1/2 MS-liquid media containing 70 µM cadmium or 0.7 mM lead. After 2 weeks, growth, weight, and heavy metal contents were measured.

(5-1) Growth of Plants

Figure 6:
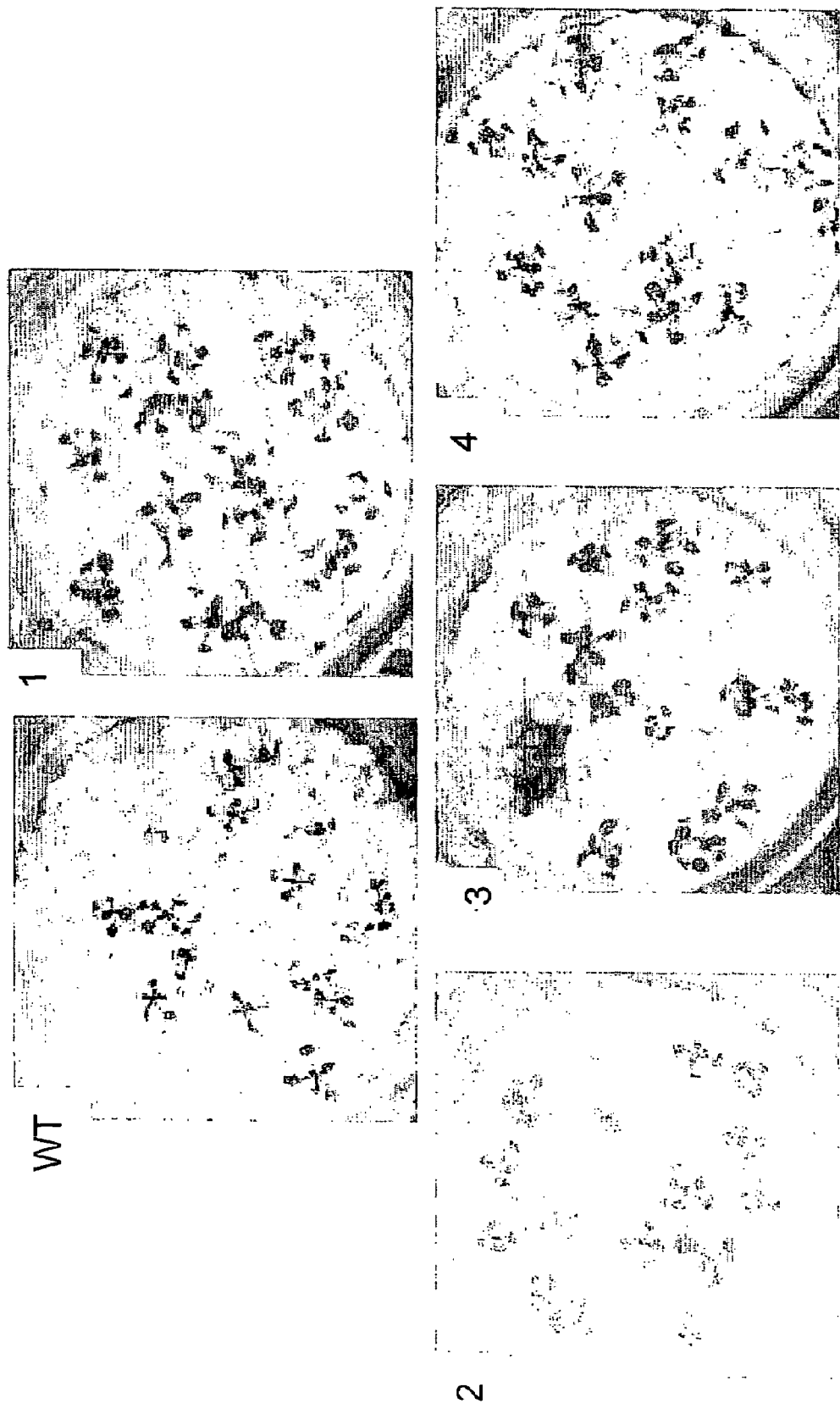
FIG. 6 shows the enhanced growth of zntA-transgenic plants over that of wild type in a medium containing lead.
Figure 7:
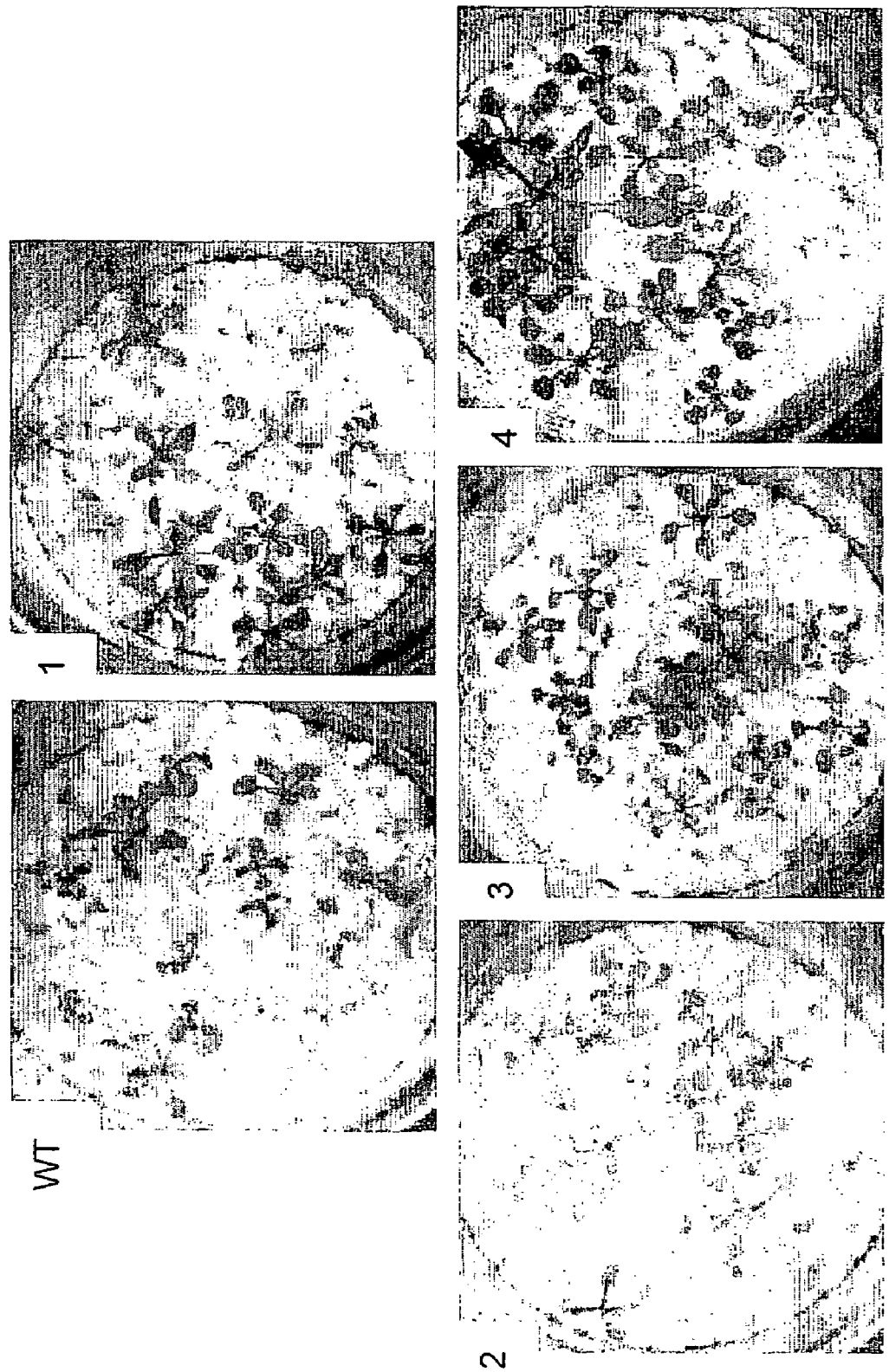
FIG. 7 shows the enhanced growth of zntA-transgenic plants over that of wild type in a medium containing cadmium.

FIG. 6 shows the growth of wild-type and pBI121/zntA *Arabidopsis* plants grown in a medium containing lead. FIG. 7 shows wild-type and pBI121/zntA *Arabidopsis* plants grown in a medium containing cadmium. "WT" is wild-type *Arabidopsis*, "1" to "4" are pBI121/zntA plants. In FIGS. 6 and 7, pBI121/zntA plants grew better than the wild-type plants; their leaves were broader, greener, and their fresh weights were higher than those of the wild types. These results indicate that the expression of ZntA confers Pb(II)- and Cd(II)-resistance to the transgenic plants.

(5-2) Measurement of Biomass

Wild type and pBI121/zntA *Arabidopsis* plants were grown in 1/2 MS-agar media for 2 weeks and then transferred to 1/2 MS-liquid media supported by small gravel with or without Cd (II) or Pb (II). After growing for an additional 2 weeks, the plants were harvested. They were washed in an ice-cold 1 mM tartarate solution and blot-dried. The weight of the wild type and pBI121/zntA *Arabidopsis* plants were measured.

Figure 8A:
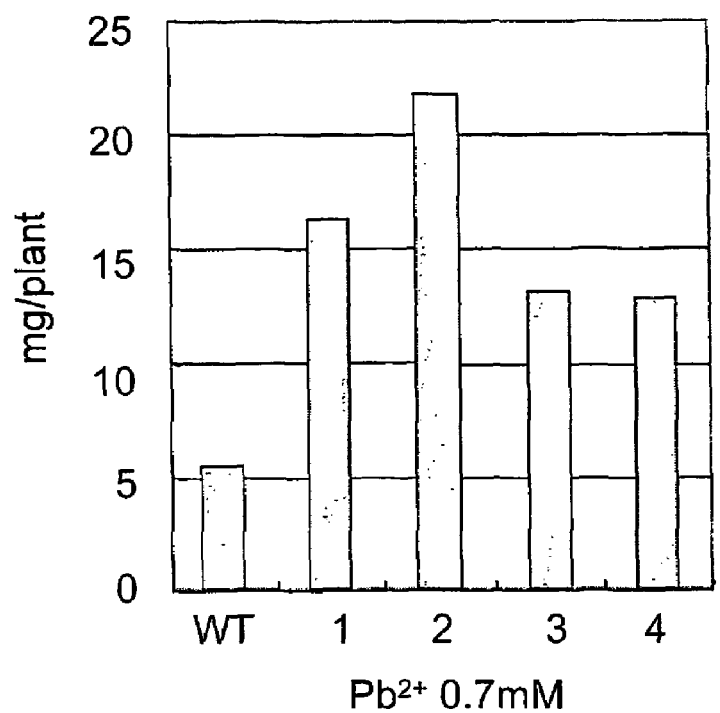
FIG. 8 is a graph showing the weight of zntA-transgenic pants cultivated in media containing heavy metals.
Figure 8B:
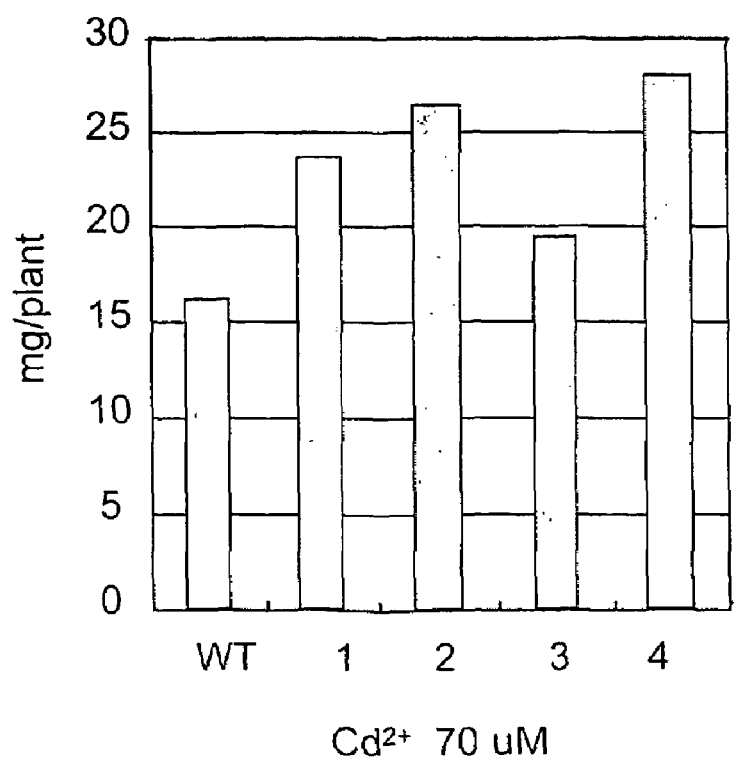

FIG. 8a is a graph showing the weight of wild type and pBI121/zntA plants grown in a medium containing lead, and FIG. 8b is a graph showing the weight of wild type and pBI121/zntA plants grown in a medium containing cadmium. The weight of pBI121/zntA plants was higher than that of the wild-type plants. These results indicate that plants expressing ZntA protein can grow better than wild type in soil contaminated with heavy metals.

(5-3) Measurement of Chlorophyll Contents

For determination of chlorophyll contents, the leaves were harvested and extracted with 95% ethanol for 20 min at 80° C. Absorbance at 664 nm and 648 nm were measured and then the chlorophyll A and B contents were calculated as described (Oh S A, Park J H, Lee G I, Paek K H, Park S K, Nam H G (1997) Identification of three genetic loci controlling leaf senescence in *Arabidopsis thaliana*. Plant J. 12, 527–35).

Figure 9A:
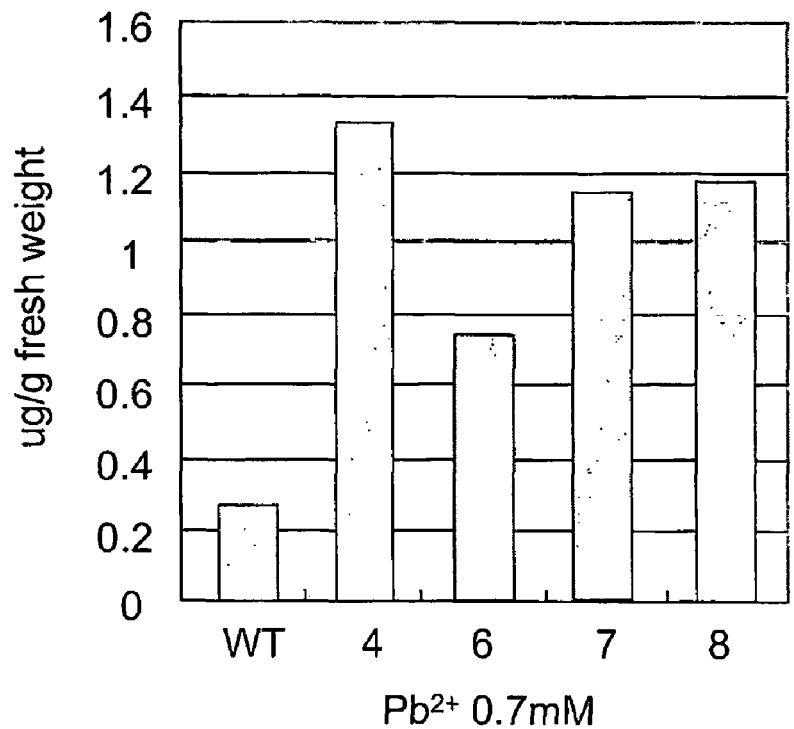
FIG. 9 is a graph showing the chlorophyll contents of zntA-transgenic and wild type plants, grown in media containing heavy metals.
Figure 9B:
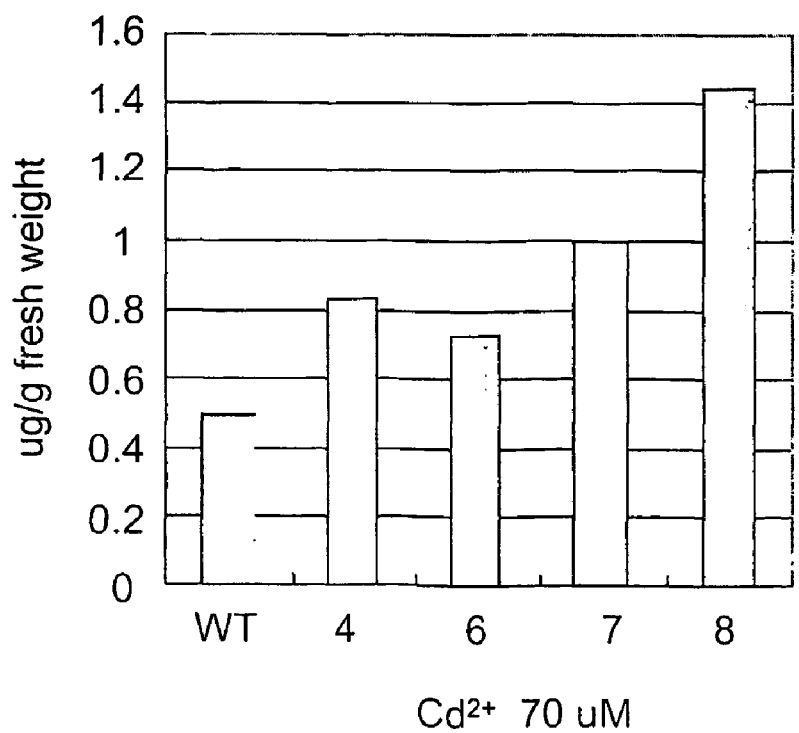

FIG. 9a is a graph showing the chlorophyll contents of wild type and zntA-transgenic plants grown in a medium containing lead, and FIG. 9b is a graph showing the chlorophyll contents of wild type and zntA-transgenic plants grown in a medium containing cadmium. The chlorophyll contents of zntA-transgenic plants were higher than those of the wild types.

(5-4) Measurement of the Heavy Metal Contents

We measured the content of Pb and Cd in control and ZntA overexpressing plants grown in media containing heavy metals. pBI121/zntA plants were collected, weighed, and digested with 65% $HNO_3$ at 200° C., overnight.

Digested samples were diluted with 0.5 N HNO$_3$ and analyzed using an atomic absorption spectrometer (AAS; SpectrAA-800, Varian).

Figure 10A:
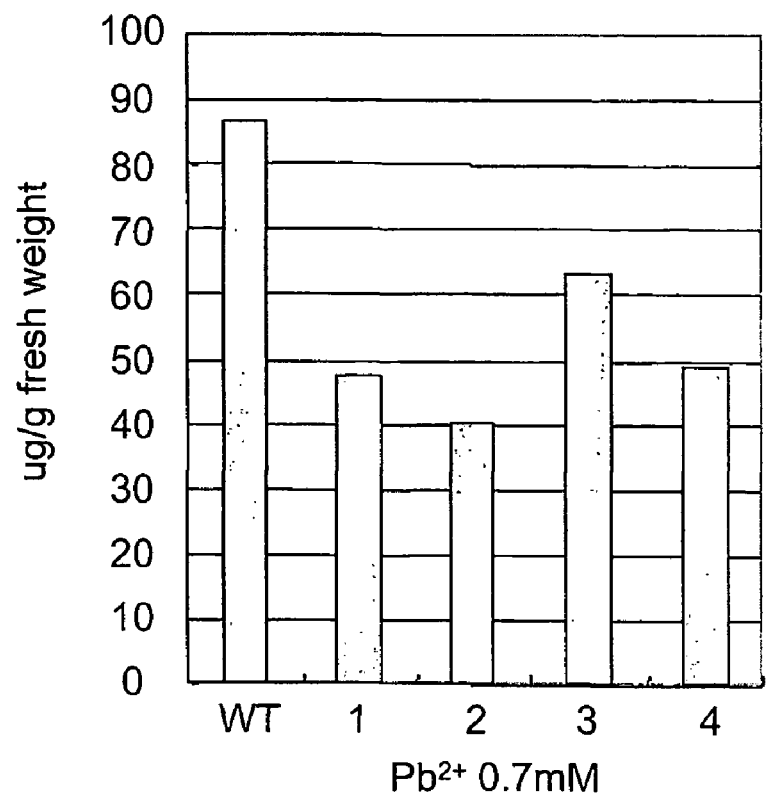
FIG. 10 is a graph showing the heavy metal contents of zntA-transgenic and wild type plants, grown in media containing heavy metals.
Figure 10B:
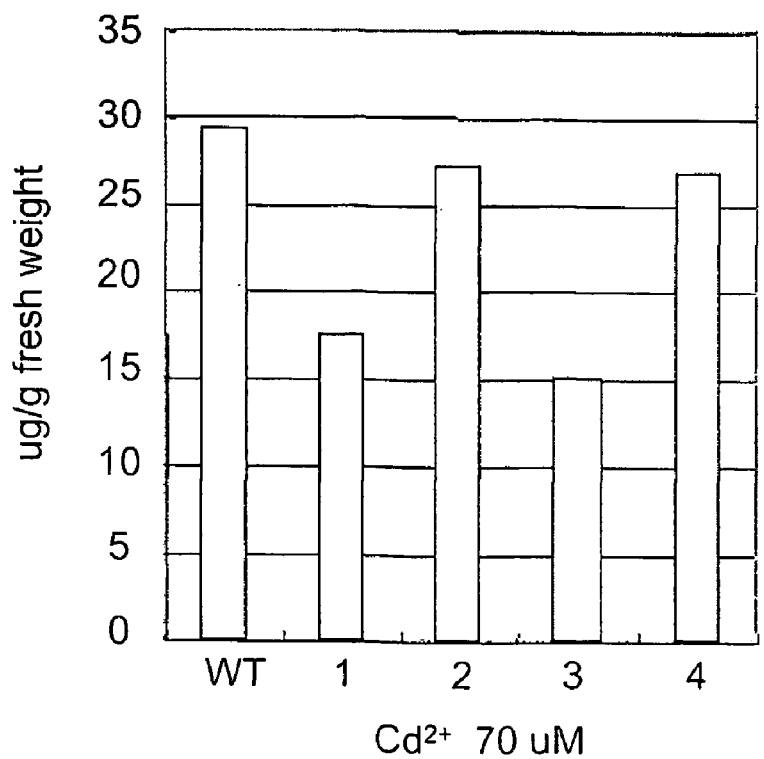

FIG. 10 is a graph showing the heavy metal contents of wild type and zntA-transgenic plants grown in media containing heavy metals. FIG. 10a is the lead contents, and 10b is the cadmium contents. Pb content of pBI121/zntA plants varied between the lines, but it was consistently lower than that of the wild type. Cd content in transgenic lines 1 and 3 was lower than that in the control.

Thus, plants transformed with zntA or other biologically active ZntA-like heavy metal pumping ATPases can be grown in soil contaminated with heavy metals and have less uptake of heavy metals than wild type plants. Since growing plants can hold contaminated soil and thereby reduce erosion of the soil, and since the zntA-transgenic plants can grow better than wild type plants in soil contaminated by heavy metals, they can reduce migration of pollutants from the polluted area, thereby reducing contamination of groundwater by the pollutants. The present invention can also be applied to crop plants to produce low heavy metal-containing safe crop plants.

What is claimed is:

1. A method of producing a transformed plant or part thereof comprising transforming the plant or part thereof with a recombinant vector comprising a nucleic acid sequence encoding ZntA having the amino acid sequence of SEQ ID NO:2, wherein the nucleic acid sequence is operably linked to a plant-expressible regulatory sequence.

2. The method according to claim 1, wherein the nucleic acid sequence comprises SEQ ID NO: 1.

3. The method according to claim 1, wherein the recombinant vector is PBI121/zntA.

4. A transgenic plant or part thereof with enhanced resistance to a heavy metal produced by the method of claim 1.

5. The transgenic plant or part thereof according to claim 4, wherein the heavy metal is at least one selected from the group consisting of arsenic, antimony, lead, mercury, cadmium, chrome, tin, zinc, barium, nickel, bismuth, cobalt, manganese, iron, copper, and vanadium.

6. A transgenic plant cell with enhanced resistance to a heavy metal, transformed with the a recombinant vector comprising a nucleic add sequence encoding ZntA having the amino acid sequence of SEQ ID NO:2.

7. The transgenic plant cell according to claim 6, wherein the heavy metal is at least one selected from the group consisting of arsenic, antimony, lead, mercury, cadmium, chrome, tin, zinc, barium, nickel, bismuth, cobalt, manganese, iron, copper, and vanadium.

8. A transgenic plant with enhanced resistance to a heavy metal, stably transformed with a recombinant vector comprising a nucleic acid sequence encoding ZntA having the amino acid sequence of SEQ ID NO:2.

9. The transgenic plant according to claim 8, wherein the heavy metal is at least one selected from the group consisting of arsenic, antimony, lead, mercury, cadmium, chrome, tin, zinc, barium, nickel, bismuth, cobalt, manganese, iron, copper, and vanadium.

10. A transgenic plant or part thereof with enhanced resistance to a heavy metal, each transformed with a recombinant vector comprising the nucleic acid sequence of SEQ ID NO:1 operably linked to a plant-expressible regulatory sequence.

11. The transgenic plant or part thereof according to claim 10, wherein the heavy metal is at least one selected from the group consisting of arsenic, antimony, Lead, mercury, cadmium, chrome, tin, zinc, barium, nickel, bismuth, cobalt manganese, iron, copper, and vanadium.

12. A transgenic plant cell with enhanced resistance to a heavy metal, transformed with a recombinant vector comprising the nucleic acid sequence of SEQ ID NO:1 operably linked to a plant-expressible regulatory sequence.

13. The transgenic plant cell according to claim 12, wherein the heavy metal is at least one selected from the group consisting of arsenic, antimony, lead, mercury, cadmium, chrome, tin, zinc, barium, nickel, bismuth, cobalt, manganese, iron, copper, and vanadium.

14. A transgenic plant with enhanced resistance to a heavy metal, stably transformed with a recombinant vector comprising the nucleic acid sequence of SEQ ID NO:1 operably linked to a plant-expressible regulatory sequence.

15. The transgenic plant according to claim 14, wherein the heavy metal is at least one selected from the group consisting of arsenic, antimony, lead, mercury, cadmium, chrome, tin, zinc, barium, nickel, bismuth, cobalt, manganese, iron, copper, and vanadium.

16. A method of producing a transgenic plant cell or transgenic plant tissue with enhanced resistance to heavy metals comprising: (a) preparing an expression construct comprising a nucleic acid sequence encoding ZntA protein having the amino add sequence of SEQ ID NO: 2, operably linked to a plant-expressible regulatory sequence; (b) preparing a recombinant vector harboring the expression construct, and (c) introducing the expression construct of the recombinant vector into a plant cell or plant tissue to produce a transgenic plant cell or transgenic plant tissue.

17. The method according to claim 16, wherein the heavy metal is at least one selected from the group consisting of arsenic, antimony, lead, mercury, cadmium, chrome, tin, zinc, barium, nickel, bismuth, cobalt, manganese, iron, copper, and vanadium.

18. The method according to claim 16, further comprising the step of:

regenerating a transgenic plant from the transgenic plant cell or transgenic plant tissue of step (c).

* * * * *